(12) United States Patent
Kleinman

(10) Patent No.: US 6,384,236 B1
(45) Date of Patent: May 7, 2002

(54) N-(AROYL)GLYCINE HYDROXAMIC ACID DERIVATIVES AND RELATED COMPOUNDS

(75) Inventor: Edward F. Kleinman, Pawcatuck, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/769,702

(22) Filed: Jan. 25, 2001

Related U.S. Application Data

(62) Division of application No. 09/011,462, filed on Jul. 6, 1998, now Pat. No. 6,225,351, which is a continuation of application No. PCT/IB96/00451, filed on May 24, 1996.
(60) Provisional application No. 60/001,524, filed on Jul. 26, 1995, now abandoned.

(51) Int. Cl.$^7$ ........................ C07D 207/06; A61K 31/40
(52) U.S. Cl. ........................ 548/539; 514/423; 514/563; 514/575; 514/567; 560/312; 560/442; 560/452; 560/621; 562/444; 562/621
(58) Field of Search ................ 514/563, 567, 514/575, 42, 423; 560/312, 442, 452, 621; 562/444, 621; 548/539

(56) References Cited

U.S. PATENT DOCUMENTS

| | | | |
|---|---|---|---|
| 3,692,827 A | 9/1972 | Garzia | |
| 3,732,295 A | 5/1973 | Dompe | |
| 3,927,082 A | 12/1975 | Katori et al. | |
| 4,193,926 A | 3/1980 | Schmiechen | 260/326.5 |
| 4,728,670 A | 3/1988 | Haglanger | 514/484 |
| 5,011,854 A | 4/1991 | Takahashi | 514/541 |
| 5,064,854 A | 11/1991 | Huth | 514/424 |
| 5,068,251 A | 11/1991 | Brooks | 514/506 |
| 5,124,455 A | 6/1992 | Lombardo | 546/181 |
| 5,256,789 A | 10/1993 | Stevens | 514/311 |
| 5,332,735 A | 7/1994 | Rault et al. | |

FOREIGN PATENT DOCUMENTS

| | | |
|---|---|---|
| WO | 9325517 | 12/1993 |
| WO | 9402465 | 2/1994 |

OTHER PUBLICATIONS

Smith et al, J. Heterocyclic Chem., vol. 26, pp 1815–1817, 1989.*
Ashton, —J.Med. Chem. 37,1696–1703 (1994).
R. D. Pace, & G.W. Kabalka, —J. Org. Chem. 60, 4838–4844 (1995).
F.T. Smith, et al. —J. Heterocyclic Chem 26, 1815–1817 (1989).
Soleim,et al., Xenobiotica, 6(3), pp 137–150 (1976).
Stafford—J. Med. Chem., 38,4972–4975 (1995).

* cited by examiner

*Primary Examiner*—Shailendra Kumar
(74) *Attorney, Agent, or Firm*—Peter C. Richardson; Paul H. Ginsburg; Raymond M. Speer

(57) ABSTRACT

Compounds of formula (I)

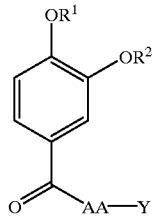

(I)

and pharmaceutically acceptable salts thereof, wherein $R^1$, $R^2$, AA and Y are as defined herein, inhibit phosphodiesterase type IV or inhibit the production of tumor necrosis factor, and therefore are useful in the treatment of certain conditions and diseases including asthma, arthritis, and sepsis.

9 Claims, No Drawings

N-(AROYL)GLYCINE HYDROXAMIC ACID DERIVATIVES AND RELATED COMPOUNDS

This application is a Div of Ser. No. 09/011,462, filed Jul. 6, 1998, now U.S. Pat. No. 6,225,351, which is a continuation of Ser. No. 60/001,524, filed Jul. 26, 1995, abandoned, and a 371 of PCT/JB96/00451, filed May, 24, 1996.

BACKGROUND OF THE INVENTION

The present invention relates to N-(aroyl)glycine hydroxamic acid derivatives and related compounds that are selective inhibitors of phosphodiesterase (PDE) type IV or of the production of tumor necrosis factor (TNF) and as such are useful in the treatment of asthma, arthritis, bronchitis, chronic obstructive airways disease, psoriasis, allergic rhinitis, dermatitis and other inflammatory diseases as well as AIDS, sepsis, septic shock, cachexia, and other diseases involving the production of TNF. The compounds of this invention may have combined PDE type IV and TNF inhibitory activity. The present invention also relates to the use of such compounds in the treatment of the above diseases in mammals, particularly humans, and to pharmaceutical compositions useful therefor.

Since the recognition that cyclic AMP is an intracellular second messenger (E. W. Sutherland, and T. W. Rall, *Pharmacol. Ref.*, 1960, 12, 265), inhibition of the phosphodiesterases has been a target for modulation and, accordingly, therapeutic intervention in a range of disease processes. More recently, distinct classes of PDE have been recognized (J. A. Beavo and D. H. Reifsnyder, *TIPS*, 1990, 11, 150), and their selective inhibition has led to improved drug therapy (C. D. Nicholson, R. A. Challiss and M. Shahid, *TIPS*, 1991, 12, 19). More particularly, it has been recognized that inhibition of PDE type IV can lead to inhibition of inflammatory mediator release (M. W. Verghese et al., *J. Mol. Cell Cardiol.*, 1989, 12, (Suppl. II), S 61) and airway smooth muscle relaxation (T. J. Torphy in *Directions for New Anti-Asthma Drugs*, eds S. R. O'Donnell and C. G. A. Persson, 1988, 37, Birkhauser-Verlag). Thus, compounds that inhibit PDE type IV, but which have poor activity against other PDE types, inhibit the release of inflammatory mediators and relax airway smooth muscle without causing cardiovascular effects or antiplatelet effects.

TNF is recognized to be involved in many infectious and auto-immune diseases, including cachexia (W. Friers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62, S 11).

SUMMARY OF THE INVENTION

The invention relates to compounds of formula

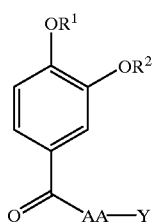

I or a pharmaceutically acceptable salt thereof, wherein
$R^1$ is selected from the group consisting of methyl, ethyl, difluoromethyl and trifluoromethyl;

$R^2$ is $(C_1-C_6)$alkyl, $(C_3-C_7)$alkoxy$(C_2-C_4)$alkyl, phenoxy$(C_2-C_6)$alkyl, $(C_3-C_7)$cycloalkyl, $(C_6-C_9)$ polycycloalkyl, phenyl$(C_1-C_8)$alkyl or indanyl wherein the alkyl portion of said $R^2$ groups is optionally substituted with one or more fluorine atoms and the aromatic portion of said $R^2$ groups is optionally substituted with one or more substituents independently selected from the group consisting of $(C_1-C_4)$alkyl, $(C_1-C_4)$alkoxy and halogen;

AA is (AA-1) or (AA-2) wherein:
(AA-1) is

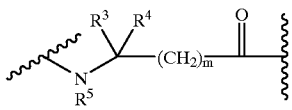

wherein $R^3$ and $R^4$ are independently selected from the group consisting of hydrogen, trifluoromethyl, $(C_1-C_6)$alkyl, $-(CH_2)_nCO_2H$, $-(CH_2)_nCONH_2$, $-(CH_2)_n$phenyl, $-(CH_2)_xOH$, and $-(CH_2)_xNH_2$, wherein x ranges from 1 to 5, n ranges from 0 to 5, $R^5$ is hydrogen, OH or $(C_1-C_6)$alkyl, and m ranges from 0 to 5; and,
(AA-2) is

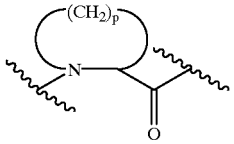

wherein p ranges from 1 to 4; and,
Y is NHOH or OH.

The term "alkyl", as used herein, unless otherwise indicated, includes saturated monovalent hydrocarbon radicals having straight or branched moieties.

The term "alkoxy", as used herein, includes O-alkyl groups wherein "alkyl" is defined above.

The term "cycloalkyl", as used herein, includes saturated monovalent cyclo hydrocarbon radicals including cyclobutyl, cyclopentyl and cycloheptyl.

The term "polycycloalkyl", as used herein, includes saturated monovalent polycyclo radicals comprising ring assemblies that are fused, bicyclo or tricyclo. Such ring assemblies include bicycloheptyl, bicyclobutyl, tricyclooctanyl and perhydropentalenyl.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1-C_6)$alkoxy, $(C_6-C_{10})$aryloxy, trifluoromethoxy, difluoromethoxy and $(C_1-C_6)$alkyl.

The term "treatment" as used herein, unless otherwise indicated, includes (i) methods to cure, relieve or lessen the undesirable effects of, or the undesirable symptoms associated with, conditions and diseases that respond to the inhibition of PDE type IV or the inhibition of the production of TNF, where such conditions and diseases are actively occurring in a mammal, including a human, and (ii) methods to prevent such conditions and diseases from occurring in a mammal, and (iii) methods to slow the onset of such conditions and diseases in a mammal. The terms "treat" and "treating" as used herein are defined in accord with the above definition.

The term "therapeutically effective amount" as used herein, unless otherwise indicated, means an amount effective to inhibit PDE type IV or inhibit the production of TNF, or an amount effective in the treatment, as defined above, of a condition or disease that responds to the inhibition of PDE type IV or the inhibition of the production of TNF.

The compounds of formula I include certain compounds having chiral centers which therefore exist in different enantiomeric forms, This invention relates to all optical isomers and stereoisomers of the compounds of formula I and mixtures thereof.

Preferred compounds of formula I include those in which $R^1$ is methyl.

Other preferred compounds of formula I include those in which $R^2$ is cyclopentyl.

Other preferred compounds of formula I include those in which AA is the moiety (i) and $R^3$ is hydrogen, methyl, trifluoromethyl or —$CH_2OH$.

Other preferred compounds of formula I include those in which AA is the moiety (AA-1) and $R^4$ is hydrogen.

Other preferred compounds of formula I include those in which AA is the moiety (AA-1) and $R^5$ is hydrogen.

Other preferred compounds of formula I include those in which AA is the moiety (AA-1) and m is 0.

Other preferred compounds of formula I include those in which Y is —NHOH.

Specific preferred compounds of formula I include the following:

α-monofluoromethyl-α-N-[(3-cyclopentyloxy-4-methoxy) benzoyl]glycine hydroxamic acid;

α-difluoromethyl-α-[(3-cyclopentyloxy-4-methoxy) benzoyl]glycine hydroxamic acid;

α-ethyl-αN-[(3-cyclopentyloxy-4-methoxy)benzoyl] glycine hydroxamic acid;

α-propyl-α-N-[(3-cyclopentyloxy-4-methoxy)benzoyl] glycine hydroxamic acid;

α-N-[(3-cyclopentyloxy-4methoxy)benzoyl]-D-cystine hydroxamic acid;

α-trifuoromethyl-α-N-[(3-cyclopentyloxy-4-methoxy) benzoyl]glycine hydroxamic acid;

α-N-[(3-cyclopentyloxy-4-methoxy)benzoyl]-D-serine hydroxamic acid;

α-N-[(3-cyclopentyloxy-4-methoxy)benzoyl]glycine hydroxamic acid; and,

α-N-[(3-cyclopentyloxy-4-methoxy)benzoyl]-D-alanine hydroxamic acid.

The present invention further relates to a pharmaceutical composition for the inhibition of PDE type IV or the inhibition of the production of TNF in a mammal, including a human, comprising a therapeutically effective amount of a compound according to formula I or a pharmaceutically acceptable salt thereof, and a pharmaceutically acceptable carrier.

The present invention further relates to a pharmaceutical composition for the treatment of a condition or disease selected from the group consisting of asthma, arthritis, bronchitis, chronic obstructive airways disease, psoriasis, allergic rhinitis, dermatitis, AIDS, septic shock and other conditions or diseases that respond to the inhibition of PDE type IV or the inhibition of the production of TNF in a mammal, including a human, comprising a therapeutically effective amount of a compound according to formula I or a pharmaceutically acceptable salt thereof, together with a pharmaceutically acceptable carrier.

The present invention further relates to a method of inhibiting PDE type IV or inhibiting the production of TNF in a mammal, comprising administering to a mammal in need of such treatment a therapeutically effective amount of a compound according to formula I or a pharmaceutically acceptable salt thereof.

The present invention further relates to a method of treating a condition or disease selected from the group consisting of asthma, arthritis, bronchitis, chronic obstructive airways disease, psoriasis, allergic rhinitis, dermatitis, AIDS, septic shock and other conditions or diseases that respond to the inhibition of PDE type IV or the inhibition of TNF in a mammal, including a human, comprising administering to a mammal in need of such treatment a therapeutically effective amount of a compound according to formula I or a pharmaceutically acceptable salt thereof.

DETAILED DESCRIPTION OF THE INVENTION

The following reaction Scheme I illustrates the preparation of the compounds of the present invention. Unless otherwise indicated, $R^1$, $R^2$, $R^3$, $R^4$, $R^5$, AA, n, m, p, and Y, as used in Scheme 1 and the following discussion, are as defined above. In Scheme 1 and the Preparations and Examples that follow, all synthesis reactions and other procedures are done at room temperature (20–25° C.) unless otherwise indicated.

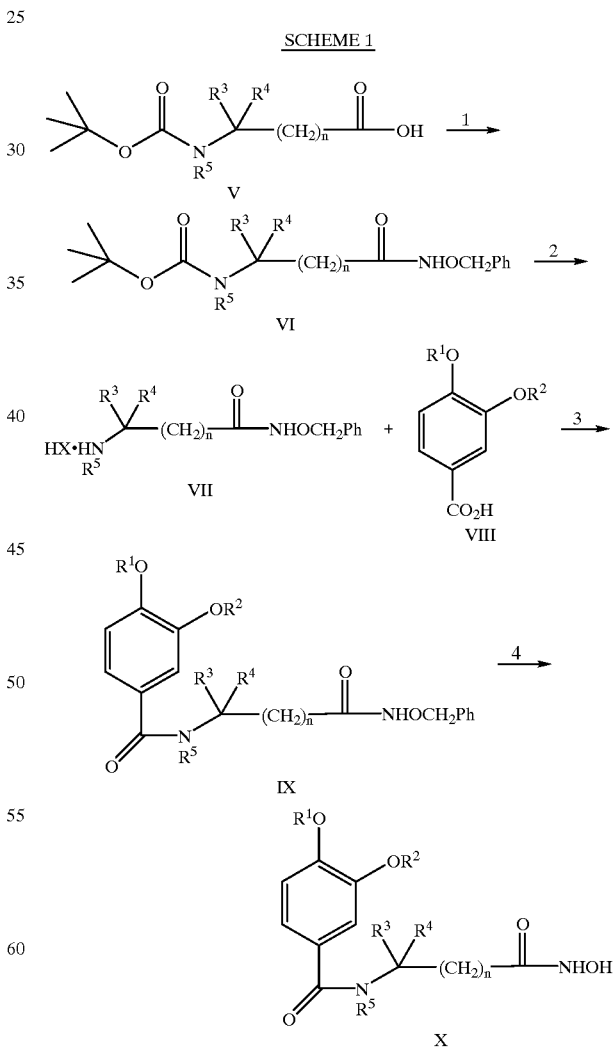

SCHEME 1

In reaction 1 of Scheme 1, a carboxylic acid of formula V is coupled to O-benzylhydroxylamine to obtain a compound of formula VI using a coupling method well known to those skilled In the art of peptide chemistry. The carboxylic acid of formula V is available from various commercial sources or can be prepared according to synthetic methods known to those skilled in the art. The preferred coupling method is to combine the compound of formula V with O-benzylhydroxylamine hydrochloride, 1-(3-dimethylaminopropyl)-3-ethylcarbodiimide hydrochloride and a base, such as triethylamine, in an inert solvent, such as methylene chloride, at a temperature of 0° C. to 30° C. (20–25° C. preferred) for a period of 2 hours to 48 hours (16 hours preferred).

In reaction 2 of Scheme 1, the compound of formula VI is treated with an acid, such as hydrochloric acid or trifluoroacetic acid, to remove the t-butyloxycarbonyl group to give a salt of formula VII, wherein X of HX is chloride or trifluoroacetate, and m, $R^3$, $R^4$ and $R^5$ are as defined above.

In reaction 3 of Scheme 1, the salt of formula VII is coupled to a benzoic acid derivative of formula VIII to prepare the compound of formula IX using a coupling method well known to those skilled in the art of peptide chemistry. The benzoic acid derivative of formula VIII can be prepared according to synthetic methods known to those skilled in the art. For instance, 3-cyclopentyloxy-4-methoxybenzoic acid can be prepared according to the method described in M. N. Palfreyman et al., *J. Med. Chem.*, vol. 37, page 1696 (1994), which is herein incorporated by reference. The preferred coupling method is to combine the compound of formula VIII with the salt of formula VII, 1-(3-dimethylaminopropyl)-3-ethylcarbodiimide hydrochloride and a base, such as triethylamine, in an inert solvent, such as methylene chloride, at a temperature of 0° C. to 30° C. (20–25° C. preferred) for a period of 2 hours to 48 hours (16 hours preferred).

In reaction 4 of Scheme 1, the compound of formula IX is hydrogenated over $Pd(OH)_2$ in a solvent such as methanol or ethanol for a period of 4 to 48 hours (16 hours preferred) to obtain the compound of formula X.

While Scheme 1 illustrates the preparation of compounds of formula I wherein AA is (AA-1), the preparation of compounds of formula I wherein AA is (AA-2) follows essentially the same route. In particular, in the first step, the compound of formula V is replaced with a compound of the same formula except the AA portion is (AA-2) rather than (AA-1). Such compounds are commercially available or can be made by synthetic techniques known to those skilled in the art. Then, reactions 1–4 are performed as described above.

To prepare compounds of formula I wherein Y is OH rather NHOH, the process begins at the third reaction of Scheme 1 where the compound of formula VII is replaced with a compound of formula XI: $HX.NHR^5CR^3R^4(CH_2)_mCO_2CH_2Ph$. Compounds of formula XI are commercially available or can be made by synthetic techniques known to those skilled in the at. The compound of formula XI is coupled with the compound of formula VIII as described above for reaction 3 of Scheme 1. Then, reaction 4 of Scheme 1 is followed as described above to prepare the compound of formula I wherein Y is OH.

Pharmaceutically acceptable acid addition salts of the compounds of this invention include, but are not limited to, those formed with acetic, lactic, succinic, maleic, tartaric, citric, gluconic, ascorbic, benzoic, cinnamic fumaric, sulfuric, phosphoric, hydrochloric, hydrobromic, toluenesulfonic, mandelic, di-p-toluoyl-1-tartaric and related acids. The acid addition salts of the compounds of formula I are prepared in a conventional manner by treating a solution or suspension of the free base of formula I with about one chemical equivalent of a pharmaceutically acceptable acid. Conventional concentration or crystallization techniques are employed in isolating the salts. Pharmaceutically acceptable cationic salts of the compounds of formula I wherein Y is hydroxyl include, but are not limited to, those of sodium, potassium, calcium, magnesium, ammonium, N,N'-dibenzylethylenediamine, N-methylglucamine (meglumine), ethanolamine and diethanolamine.

The ability of the compounds of formula I and their pharmaceutically acceptable salts to inhibit PDE type IV or inhibit the production of TNF and, consequently, demonstrate their effectiveness for treating diseases that respond to the inhibition of PDE IV or the inhibition of the production of TNF is shown by the following in vitro assay tests.

Biological Assay

Human Eosinophil PDE

Human peripheral blood is collected in ethylenediaminetetraacetic acid, diluted 1:2 in piperazine-N,N'-bis-2-ethanesulfonic acid (PIPES) buffer and then layered over percoll solution. Gradients are formed by centrifugation for 30 minutes at 2000 rpm at 40° C. The remainder of the isolation procedure, which is based on the procedure of Kita et al., J. Immunol., 152, 5457 (1994), is carried out at 4° C. The neutrophil/eosinophil layer is collected from the percoll gradient and the red blood cells are lysed. Remaining cells are washed in PIPES (1% FCS), incubated with anti-CD16 microbeads (MACS) for 1 hour, and passed over a magnetic column to remove the neutrophils. Eosinophils are collected in the eluate and analyzed for viability by trypan blue and purity by diff-quick stain. Eosinophil purity is routinely greater than 99% using this method.

Purified eosinophils are resuspended in 750 µL of PDE lysis buffer (20 mM triethylamine, 1 mM ethylenediaminetetraacetic acid, 100 µg/ml bacitracin, 2 mM benzamidine, 50 µM leupeptin, 50 µM PMSF, 100 µg/ml soybean trypsin inhibitor) and quick frozen in liquid nitrogen. Cells are thawed slowly and sonicated. Membranes are vortexed (disruption is confirmed by Trypan blue staining of fragments). Disrupted cells are centrifuged at 45 k rpm for 30 minutes at 4° C. to isolate membranes. Cytosol is decanted, and membrane resuspended to 200 µg/ml for use as PDE source in the hydrolysis assay yielding a window from 3000 to 5000 counts.

Compounds are dissolved in dimethyl sulfoxide at $10-2M$, then diluted 1:25 in water to $4\times10^{-4}$ M. This suspension is serially diluted 1:10 in 4% dimethyl sulfoxide, for a final dimethyl sulfoxide concentration in the assay of 1%.

Phosphodiesterase Inhibition Assay

To 12×75 mm glass tubes add:

25 µl PDE assay buffer (200 mM Tris/40 mM MgC12)

24 µl 4 nM/ml CAMP stock

25 µl test compound

25 µl PDE source (membrane)

Background control=membrane boiled 10'

Positive control—25 µl unboiled membrane

Incubate 25 minutes in 37° C. water bath.

Reaction is stopped by boiling samples 5 minutes. Samples are applied to Afri-gel column (1 ml bed volume) previously equilibrated with 0.25 M acetic acid followed by 0.1 mM N-[2-hydroxyethyl]piperazine-N'-2-ethanesulfonic acid (HEPES)/0.1 mM NaCl wash buffer (pH 8.5). cAMP is washed off column with HEPES/NaCl, 5'-AMP is eluted in 4 ml volumes with 0.25 M acetic acid. 1 ml of eluate is counted in 3 ml scintillation fluid for 1 minute ([3H].

Substrate conversion=(cpm positive control×4)/total activity. Conversion rate must be between 3 and 15% for experiment to be valid.

% Inhibition−1-(eluted cpm−background cpm/control cpm−bkgd cpm)×100.

$IC_{50}$ values are generated by linear regression of inhibition titer curve (linear portion); and are expressed in $\mu$M.

TNF

The ability of the compounds of formula I and the pharmaceutically acceptable salts thereof to inhibit the production of TNF and, consequently, demonstrate their effectiveness for treating diseases involving the production of TNF is shown by the following in vitro assay:

Peripheral blood (100 mls) from human volunteers is collected in ethylenediaminetetraacetic acid (EDTA). Mononuclear cells are isolated by Ficoll/Hypaque and washed three times in incomplete Hanks' balanced salt solution (HBSS). Cells are resuspended in a final concentration of $1 \times 10^6$ cells per ml in prewarmed RPMI (containing 5% FCS, glutamine, pen/step and nystatin). Monocytes are plated as $1 \times 10^6$ cells in 1.0 ml in 24-well plates. The cells are incubated at 37° C. (5% carbon dioxide) and allowed to adhere to the plates for 2 hours, after which time nonadherent cells are removed by gently washing. Test compounds (10 $\mu$l) are then added to the cells at 3–4 concentrations each and incubated for 1 hour. Lipopolysaccharide (LPS) (10 $\mu$l) is added to appropriate wells. Plates are incubated overnight (18 hrs) at 37° C. At the end of the incubation period TNF was analyzed by a sandwich ELISA (R&D Quantikine Kit). $IC_{50}$ determinations are made for each compound based on linear regression analysis.

For administration to humans in the curative or prophylactic treatment of inflammatory diseases, oral dosages of the compounds of formula I and the pharmaceutically acceptable salts thereof (hereinafter also referred to as the active compounds of the present invention) are generally in the range of from 0.1–400 mg daily for an average adult patient (70 kg). Thus for a typical adult patient, individual tablets or capsules contain from 0.1 to 50 mg of active compound, in a suitable pharmaceutically acceptable vehicle or carrier. Dosages for intravenous administration are typically within the range of 0.1 to 40 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes can be used including oral, parenteral and topical administration routes. In general, the active compound will be administered orally or parenterally at dosages between about 0.1 and 25 mg/kg body weight of the subject to be treated per day, preferably from about 0.3 to 5 mg/kg. The compound of formula I can also be administered topically in an ointment or cream in concentrations of about 0.5% to about 1%, generally applied 2 or 3 times per day to the affected area. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

The present invention is illustrated by the following preparations and examples, but it is not limited to the details thereof. In the following preparations and examples, the term "t-BOC" represents a t-butoxycarbonyl group, and the symbol "Bn" represents a benzyl group.

Preparation 1

O-Benzyl-α-N-t-BOC-glycine Hydroxamate

To a mixture of 3.0 g (0.017 mol) of α-N-(t-butoxycarbonyl)glycine, 2.7 g (0.017 mol) of O-benzylhydroxylamine hydrochloride, and 60 ml of $CH_2Cl_2$ was added 3.6 ml (2.6 g, 0.026 mol) of triethylamine followed by 5.0 g (0.026 mol) of 1-(3-dimethylaminopropyl)-3-ethylcarbodiimide. The suspension was stirred for 16 h at room temperature under $N_2$. The clear mixture was evaporated and the semi-solid residue was dissolved in 300 ml of EtOAc, washed with aqueous 1N HCl solution (2×200 ml), saturated aqueous $NaHCO_3$ solution (2×200 ml), and dried over $MgSO_4$. Removal of the drying agent by filtration and evaporation of the solvent afforded 4.3 g (90%) of the title compound as a clear oil. $R_f$ 0.2 (2:3 EtOAc-hexane). $^1$H-NMR (CDCl$_3$): δ1.37 (9H, s), 2.62 (2H, br s), 4.82 (2H, s), 5.10 (1H, br s), 7.23–7.35 (5H, m), 8.89 (1H, br s).

Preparation 2

O-Benzyl-α-N-[(3-cyclopentyloxy-4-methoxy) benzoyl]glycine Hydroxamate

A mixture of 4.3 g of the compound of Preparation 1 and 20 ml of a 4M HCl solution in dioxane was stirred for 4 hr at room temperature protected from atmospheric moisture with a $CaCl_2$ tube. At this time TLC analysis showed complete consumption of starting material, and the solvent was evaporated to give 3.2 g of O-benzyl-glycine hydroxamate hydrochloride as a gummy solid.

To a mixture of 1.35 g (6.35 mmol) of the solid above, 1.50 g (6.35 mmol) of 3-cyclopentyloxy-4-methoxybenzoic acid, and 60 ml of $CH_2Cl_2$ was added 1.33 ml (966 mg, 9.53 mmol) of triethylamine followed by 1.83 g (9.63 mmol) of 1-(3-dimethylaminopropyl)-3ethylcarbodiimide. After stirring for 16 hr at room temperature, the mixture was evaporated and the residue was dissolved in 150 ml of EtOAc, washed with aqueous 1N HCl solution (2×75 ml), saturated aqueous $NaHCO_3$ solution (2×75 ml), and dried over MgSO$_4$. The drying agent was removed by filtration, the filtrate was evaporated, and the residue was purified by flash chromatography (75 g of silica gel) using a 4:1 EtOAc-hexane eluant to give 773 mg (30%) of the title compound as a foam; R$_f$ 0.35 (EtOAc). $^1$H-NMR (DMSO-d$^6$): δ1.44–2.00 (9H, m), 3.75 (5H, br s), 4.70–4.82 (1H, m), 4.74 (2H, s), 6.95 (1H, d, J=8), 7.22–7.46 (7H, m), 8.54 (1H, m).

Preparations 3–16

The following compounds, having a structure of formula II, were prepared in accord with the procedure of Preparation 1 except using as starting materials an α-N-t-BOC-AA-OH amino acid, wherein M is as defined in Table 1, in place of α-N-t-BOC-glycine.

α-N-t-BOC-AA-NHOBn

TABLE 1

| Preparation No. | AA | Melting Point (° C.) | Data |
|---|---|---|---|
| 3 | (structure: N(Me)CH$_2$C(O)) | 103–105 | $^1$H-NMR(CDCl$_3$): δ1.43(9H, s), 2.91(3H, s), 3.91(2H, br s), 3.92 (2H, s), 7.36–7.43(5H, m) |
| 4 | (structure: NH-CH(CH$_3$)-C(O), stereo) | 101–103 | $^1$H-NMR(CDCl$_3$): δ1.31(3H, d, J=8), 1.40(3H, s), 3.90–4.03(1H, m), 4.80–4.92(1H, br s), 4.89 (2H, s), 7.25–7.35(5H, s), 8.78–8.96(1H, br s) |
| 5 | (structure: NH-CH(CH$_3$)-C(O), stereo) | 102–104 | $^1$H-NMR(CDCl$_3$): δ1.29(3H, d, J=8), 1.38(9H, s), 3.88–4.01(1H, m), 4.78–4.92(1H, br s), 4.85 (2H, s), 7.20–7.36(5H, s), 8.75–9.00(1H, br s) |
| 6 | (structure: NH-CH$_2$-CH$_2$-C(O)) | 107–109 | $^1$H-NMR(CDCl$_3$): δ1.44(9H, s), 2.21–2.65(2H, m), 2.41(2H, q, J=7), 4.76–5.07(3H, m), 7.33–7.44(5H, m), 8.27(1H, br s) |
| 7 | (structure: NH-C(CH$_3$)$_2$-C(O)) | 134–136 | $^1$H-NMR(CDCl$_3$): δ1.36(9H, s), 1.42(6H, s), 4.66(1H, br s), 4.86 (2H, s), 7.26–7.37(5H, m), 9.30 (br s) |
| 8 | (structure: NH-CH(CF$_3$)-C(O)) | — | $^1$H-NMR(CDCl$_3$): δ1.37(9H, s), 4.60–4.76(1H, m), 4.85(2H, s), 5.56–5.84(1H, br s), 5.26–7.35 (5H, m), 8.97(1H, br s) |
| 9 | (structure: isobutyl-CH-NH-C(O), leucine) | oil | $^1$H-NMR(CDCl$_3$): δ0.86(8H, d, J=7), 1.37(9H, s), 1.50–1.67(3H, m), 3.80–3.90(1H, m), 4.70–4.81 (1H, m), 4.85(2H, s), 7.25–7.36 (5H, m), 8.70(1H, br s) |
| 10 | (structure: isobutyl-CH-NH-C(O), leucine) | oil | $^1$H-NMR(CDCl$_3$): δ0.80(6H, d, J=7), 1.31(9H, s), 1.44–1.60(3H, m), 3.76–3.88(1H, m), 4.68–4.80 (1H, m), 4.79(2H, s), 7.20–7.30 (5H, m), 8.77(1H, br s) |

TABLE 1-continued

| Preparation No. | AA | Melting Point (° C.) | Data |
|---|---|---|---|
| 11 | | 127–129 | $^1$H-NMR(CDCl$_3$): δ0.93(6H, d, J=7), 1.43(9H, s), 1.99–2.12(1H, m), 3.62–3.72(1H, m), 4.91(2H, s), 4.98–5.10, 7.30–7.42(5H, m), 8.80(1H, s) |
| 12 | | 128–130 | $^1$H-NMR(CDCl$_3$): δ0.93(6H, d, J=7), 1.44(9H, s), 1.99–2.13(1H, m), 3.60–3.73(1H, m), 4.92(2H, s), 4.98–5.10(1H, m), 7.30–7.43 (5H, m), 8.77(1H, br s) |
| 13 | | 90–92 | $^1$H-NMR(CDCl$_3$): δ1.40(9H, s), 2.86–3.00(1H, br s), 3.52–3.64 (1H, m), 3.92–4.10(2H, m), 3.89 (2H, s), 5.44–5.56(1H, m), 7.26–7.38(5H, m), 9.20(1H, br s) |
| 14 | | 84–86 | $^1$H-NMR(CDCl$_3$): δ1.40(9H, s), 3.05–3.15(1H, br s), 3.50–3.63 (1H, m), 3.92–4.03(2H, m), 3.89 (2H, s), 5.46–5.56(1H, m), 7.28–7.40(5H, m), 9.33(1H, br s) |
| 15 | | 186–187 | Anal. Calculated formula C$_{17}$H$_{24}$N$_2$O$_4$: C, 63.96; H, 7.80; N, 8.87. Found: C, 63.95; H, 7.80; N, 8.87 |
| 16 | | 187–188 | Anal. Calculated formula C$_{17}$H$_{24}$N$_2$O$_4$: C, 63.96; H, 7.80; N, 8.87. Found: C, 63.91; H, 7.76; N, 8.94 |

Preparation 17

O-Benzyl-(3-Cyclopentyloxy-4-methoxy) benzoylhydroxamate

Following the procedure of Preparation 1 except substituting 3-cycopentyloxy-4-methoxybenzoic acid for α-N-t-BOC-glycine, the title compound was prepared as fluffy crystals after recrystallization from hexane/CH$_2$C$_2$, m.p. 120.5–121° C. Anal. Calculated formula C$_{20}$H$_{23}$NO$_4$: C, 70.36; H, 6.79; N, 4.10. Found: C, 70.31; H, 6.97; N, 4.43.

Preparation 18 t-Butyl-α-N-benzyloxy-α-N-[(3-cyclopenteloxy-4-methoxy)benzoyl]glycinate

To a dry 25 ml 3-necked flash under N$_2$ was placed 77.8 mg (1.62 mmol) of 50% NaH in mineral oil which was subsequently washed with hexane. The bare hydride was suspended in 1 ml of tetrahydrofuran (hereinafter "THF") and treated dropwise with a solution of 504 mg (1.48 mmol) of the compound of Preparation 17 in 4 ml of THF. After the H$_2$ evolution had ceased and the mixture became clear, 261 μl (315 mg, 1.62 mmol) of t-butyl acetate was added. An additional 447 μl of t-butyl acetate was added 2 hours later. After stirring for 16 hours at room temperature, the mixture was diluted with 50 ml of ether, washed with H$_2$O (1×30 ml), 1N NaOH solution (3×30 ml), dried (MgSO$_4$), and evaporated to 846 mg of an oil.

Purification of the oil by flash chromatography (70 g of silica gel) using 20% EtOAc-hexane as eluant gave 476 mg of an oil which spontaneously crystallized. Trituration in hexane gave 392 mg a white solid, m.p. 87–89° C., which was recrystallized from hexane to yield 302 mg of the title compound as white needles, m.p. 88–90° C. Anal. Calculated formula C$_{26}$H$_{33}$NO$_6$: C, 68.55; H, 7.30; N, 3.07. Found: C, 68.84; H, 7.57; N, 3.02.

Preparation 19

O-Benzyl-α-N-benzyloxy-α-N-[(3-cyclopentyloxy-4-methoxy)benzoyl]glycine Hydroxamate A mixture of 1.64 g (4.11 mmol) of the compound of Preparation 18 and 20 ml of trifluoroacetic acid was stirred at room temperature for 45 min using a CaCl$_2$ drying tube. The mixture was evaporated and the residue was dissolved in 100 ml of ether, washed with H$_2$O (3×75 ml), brine (1×75 ml), dried (MgSO$_4$), and evaporated to give 1.42 g of α-N-benzyloxy-α-N-[3-cyclopentyloxy-4-methoxy)benzoyl]glycine. $^1$H-NMR (CDCl$_3$): δ1.52–1.97 (8H, m), 3.88 (3H, s), 4.50 (2H, s), 4.68–4.75 (1H, m), 4.78 (2H, s), 6.84 (1H, d, J=8), 7.12–7.42 (7H, m), 9.02 (1H, br s).

The title compound was prepared as a foam in analogy to the procedure of Preparation 1 substituting the above acid for α-N-(t-butoxycarbonyl)glycine. $^1$H-NMR (CDCl$_3$): δ1.48–1.95 (8H, m), 3.88 (3H, s), 4.38 (2H, s), 4.58–4.68 (1H, m), 4.69 (2H, s), 4.93 (2H, s), 6.83 (1H, d, J=8), 7.07–7.16 (2H, m), 7.23–7.42 (10H, m), 9.27 (1H, s).

Preparations 20—33

The following compounds, having the structure of formula III, were prepared in accord with the procedure of Preparation 2 except using as starting material the compounds from the indicated Preparations in place of the compound of Preparation 1.

TABLE 2

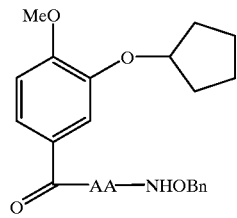

III

| Preparation No. | AA | Starting Material - Compound Of Preparation No. | Melting Point (° C.) | Data |
|---|---|---|---|---|
| 20 | ![N(Me)CH2C(O)] | 3 | oil | $^1$H-NMR(CDCl$_3$): δ 1.50–1.95(8H, m), 3.07 (3H, s), 3.85(3H, s), 3.95(2H, s), 4.68–4.78 (1H, m), 4.91(2H, s), 6.79(1H, d, J=8), 6.84–7.40(7H, m), 9.44(1H, br s) |
| 21 | ![NH-CH(Me)-C(O)] | 4 | 161–163 | Anal. Calculated formula C$_{23}$H$_{28}$N$_2$O$_5$: C, 66.97; H, 6.84; N, 6.79. Found: 66.77; H, 7.02; N, 6.87 |
| 22 | ![NH-CH(Me)-C(O)] | 5 | 163–165 | $^1$H-NMR(DMSO-d$^6$): δ 1.31(3H, d, J=7), 1.50–1.96(8H, m), 3.82(3H, s), 4.35(1H, br t), 4.81 (2H, s), 4.82–4.90(1H, m), 7.21(1H, d, J=8), 7.32–7.56(7H, m), 8.39 (1H, d, J=7) |
| 23 | ![NH-CH2CH2-C(O)] | 6 | 148–149 | Anal. Calculated formula C$_{23}$H$_{28}$N$_2$O$_5$: C, 66.97; H, 6.84; N, 6.79. Found: 66.58; H, 7.12; N, 6.74 |
| 24 | ![NH-C(Me)2-C(O)] | 7 | 135–137 | Anal. Calculated formula C$_{24}$H$_{30}$N$_2$O$_5$: C, 67.58; H, 7.09; N, 6.57. Found: C, 67.31; H, 6.68; N, 6.80 |

TABLE 2-continued

Structure III: 3-cyclopentyloxy-4-methoxybenzoyl—AA—NHOBn

| Preparation No. | AA | Starting Material - Compound Of Preparation No. | Melting Point (° C.) | Data |
|---|---|---|---|---|
| 25 | —NH—CH(CH₂CF₃)—C(=O)— (α-CF₃ substituted aminoacyl) | 8 | Oil | ¹H-NMR(CDCl₃): δ 1.46–1.96(5H, m), 3.85 (3H, s), 4.68–4.76(1H, m), 4.87(2H, s), 4.35–4.45(1H, m), 6.80(1H, d, J=8), 7.10(1H, d, J=8), 7.18–7.38(6H, m), 9.89(1H, s) |
| 26 | Leucyl | 9 | 140–142 | Anal. Calculated formula C₂₆H₃₄N₂O₅: C, 68.70; H, 7.54; N, 6.16. Found: C, 68.36; H, 7.69; N, 6.37 |
| 27 | Leucyl | 10 | 142–144 | Anal. Calculated formula C₂₆H₃₄N₂O₅: C, 68.70; H, 7.54; N, 6.16. Found: C, 68.46; H, 7.72; N, 6.31 |
| 28 | Valyl | 11 | 173–176 | Anal. Calculated formula C₂₅H₃₂N₂O₅: C, 68.16; H, 7.32; N, 6.36. Found: C, 67.88; H, 7.30; N, 6.48 |
| 29 | Valyl | 12 | 173–176 | Anal. Calculated formula C₂₅H₃₂N₂O₅: C, 68.16; H, 7.32; N, 6.36. Found: C, 67.88; H, 7.33; N, 6.50 |
| 30 | Seryl | 13 | 122–124 | Anal. Calculated formula C₂₃H₂₈N₂O₆·¼H₂O: C, 63.74; H, 6.60; N, 6.47. Found: 63.37; H, 7.02; N, 6.83 |

TABLE 2-continued

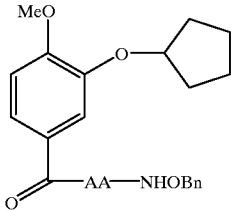

III

| Preparation No. | AA | Starting Material - Compound Of Preparation No. | Melting Point (° C.) | Data |
|---|---|---|---|---|
| 31 | 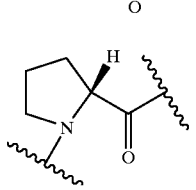 | 14 | 144–148 | Anal. Calculated formula $C_{23}H_{28}N_2O_6 \cdot \frac{1}{4}H_2O$: C, 63.74; H, 6.60; N, 6.47. Found: 63.73; H, 6.56; N, 6.52 |
| 32 | 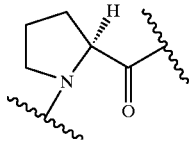 | 15 | foam | $^1$H-NMR(DMSO-d$^6$): δ 1.41–2.18(12H, m), 3.40–3.63(2H, m), 3.75 (3H, s), 4.05–4.28(1H, m), 4.37–4.63(1H, m), 4.75(2H, s), 6.80–7.38 (8H, m), 8.25(1H, s) |
| 33 | 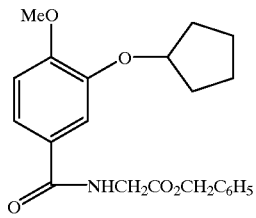 | 16 | foam | $^1$H-NMR(DMSO-d$^6$): δ 1.42–2.10(12H, m), 3.36–3.58(2H, m), 3.71 (3H, s), 4.03–4.25(1H, m), 4.35–4.58(1H, m), 4.70(2H, s), 6.76–7.35 (8H, m), 8.20(1H, s) |

Preparation 34

N-[(3-Cyclopentyl-4-methoxy)benzoyl]glycine Benzyl Ester

To a mixture of 0.500 g (2.12 mmol) of 3-cyclopentyl-4-methoxybenzoic acid and 0.470 g (2.33 mmol) of glycine benzyl ester hydrochloride in 20 ml of $CH_2Cl_2$ was added 0.410 g (2.12 mmol) of 1-(3-dimethylaminopropyl)-3-ethylcarbodiimide hydrochloride followed by 0.236 g (2.33 mmol) of trethylamine. The mixture was stirred for 16 hours at room temperature.

The solvent was evaporated and the residue was diluted with water (150 ml) and extracted with ether (2×150 ml). The combined other extracts were washed with aqueous 1N HCl (1×50 ml), saturated aqueous $NaHCO_3$, dried ($MgSO_4$), and evaporated to 940 mg of a white solid. Purification by flash chromatography (55 g of silica gel) using a 3:7 EtOAc:hexane eluant afforded 518 mg of the title compound, mp 108–109° C. $^1$H NMR (CDCl$_3$): δ1.40–1.95 (8H, m), 3.85 (3H, s), 4.24 (2H, d, J=5), 4.70–4.80 (1H, m), 5.20 (2H, s), 6.50 (1H, br s), 6.83 (1H, d, J=8), 7.10–7.40 (7H, m).

EXAMPLE 1

α-N-[(3-Cyclopentyloxy-4-methoxy)benzoyl] glycine Hydroxamic Acid

A mixture of 770 mg of the compound of Preparation 2, 70 mg of Pd(OH)$_2$, and 50 ml of methanol was hydrogenated at 40 psi on a Parr Shaker apparatus for 16 hours. The catalyst was removed by filtration and the filtrate was evaporated to a solid which was triturated in ether to afford 510 mg of the title compound, m.p. 160–161° C. Anal. Calculated formula $C_{15}H_{20}N_2O_5$: C, 57.54; H, 6.55; N, 8.95. Found: C, 57.48; H, 6.51; N, 8.74.

EXAMPLES 2–16

The compounds of Examples 2–16, having the structure of formula IV, were prepared in accord with the procedure described in Example 1 except using as starting material the compounds of Preparations 19–33 rather than the compound of Preparation 2.

TABLE 3

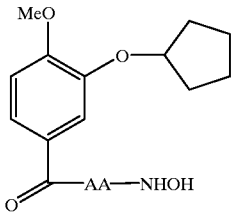

IV

| Example No. | AA | Starting Material - Compound Of Preparation No. | Melting Point (° C.) | Data |
|---|---|---|---|---|
| 2 | 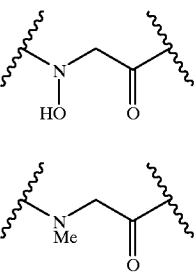 | 19 | 80–105(dec.) | Anal. Calculated formula C$_{15}$H$_{20}$N$_2$O$_6$: C, 55.55; H, 6.22; N, 8.64. Found: C, 55.40; H, 6.61; N, 8.44 |
| 3 | 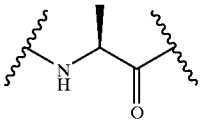 | 20 | 132–142 (dec.) | Anal. Calculated formula C$_{16}$H$_{22}$N$_2$O$_5$: C, 59.62; H, 6.88; N, 8.89. Found: C, 59.77; H, 7.10; N, 8.49 |
| 4 | 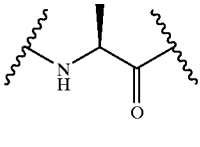 | 21 | 117–130 (dec.) | Anal. Calculated formula C$_{16}$H$_{22}$N$_2$O$_5$: C, 59.62; H, 6.88; N, 8.69. Found: C, 59.82; H, 6.99; N, 8.74 |
| 5 | 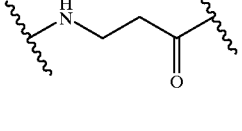 | 22 | 152–154 | Anal. Calculated formula C$_{16}$H$_{22}$N$_2$O$_5$·¼H$_2$O: C, 58.78; H, 6.94; N, 8.57. Found: C, 58.72; H, 7.03; N, 8.56 |
| 6 | 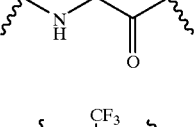 | 23 | 153–156 | Anal. Calculated formula C$_{16}$H$_{22}$N$_2$O$_5$: C, 59.62; H, 6.88; N, 8.69. Found: C, 59.37; H, 6.59; N, 8.83 |
| 7 | 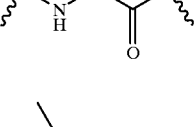 | 24 | 104–107 | Anal. Calculated formula C$_{17}$H$_{24}$N$_2$O$_5$·½H$_2$O: C, 59.06; H, 7.24; N, 8.11. Found: C, 59.14; H, 7.59; N, 7.83 |
| 8 | 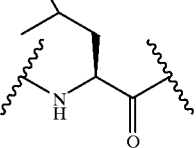 | 25 | 155–157 | LSI-MS(m/e): 377(M$^+$), 344, 276, 219 |
| 9 |  | 26 | 150–153 | Anal. Calculated formula C$_{19}$H$_{28}$N$_2$O$_5$: C, 62.62; H, 7.74; N, 7.69. Found: C, 62.95; H, 8.14; N, 7.71 |

TABLE 3-continued

[Structure IV: 4-methoxy-3-(cyclopentyloxy)benzoyl-AA-NHOH]

IV

| Example No. | AA | Starting Material - Compound Of Preparation No. | Melting Point (° C.) | Data |
|---|---|---|---|---|
| 10 | [isobutyl-CH-NH / C=O] | 27 | 151–154 | ¹H-NMR(DMSO-d⁶): δ 0.89(3H, d, J=7), 0.94 (3H, d, J=7), 1.43–2.03 (11H, m), 3.80(3H, s), 4.55(1H, br t), 4.82–4.98 (1H, m), 7.01(1H, d, J=8), 7.48(1H, s), 7.55 (1H, d, J=8), 8.22 and 8.32(1H total, two d, J=9), 8.85(0.5H, s), 10.72(0.5H, s) |
| 11 | [isopropyl-CH-NH / C=O] | 28 | 166 . 167 | Anal. Calculated formula $C_{18}H_{26}N_2O_5 \cdot \frac{1}{2}H_2O$: C, 60.10; H, 7.51; N, 7.80. Found: C, 60.21; H, 7.70; N, 7.87 |
| 12 | [isopropyl-CH-NH / C=O] | 29 | 183–186 | Anal. Calculated formula $C_{18}H_{26}N_2O_5 \cdot \frac{1}{4}H_2O$: C, 60.86; H, 7.47; N, 7.89. Found: C, 60.64; H, 7.70; N, 7.76 |
| 13 | [HOCH₂-CH-NH / C=O] | 30 | 149–152 | Anal. Calculated formula $C_{16}H_{22}N_2O_6 \cdot \frac{3}{4}H_2O$: C, 54.56; H, 6.68; N, 7.96. Found: C, 54.17; H, 6.81; N, 8.15 |
| 14 | [HOCH₂-CH-NH / C=O] | 31 | 143–147 | Anal. Calculated formula $C_{16}H_{22}N_2O_6 \cdot \frac{1}{4}H_2O$: C, 55.99; H, 6.56; N, 8.17. Found: C, 55.67; H, 6.96; N, 7.87 |
| 15 | [pyrrolidine-2-carbonyl] | 32 | 116–120 (dec.) | Anal. Calculated formula $C_{18}H_{24}N_2O_5 \cdot \frac{1}{2}H_2O$: C, 60.49; H, 7.00; N, 7.84 Found: C, 60.75; H, 7.20; N, 7.81 |

TABLE 3-continued

IV

| Example No. | AA | Starting Material - Compound Of Preparation No. | Melting Point (° C.) | Data |
|---|---|---|---|---|
| 16 | 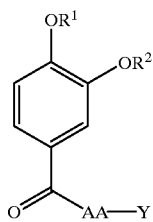 | 33 | 117–121 | $^1$H-NMR(DMSO-d$^6$): δ 1.51–2.22(10, m), 3.50 (1H, br t), 3.62(1H, br t), 3.80(3H, s), 4.33(1H, br t), 4.78–4.86(1H, m), 6.90(1H, br s), 7.00(1H, d, J=8), 7.12(1H, s), 7.15(1H, d, J=8), 11.2 (1H, s) |

EXAMPLE 17

N-[(3-Cyclopentyl-4-methoxy)benzoyl]glycine

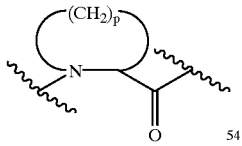

The compound of Example 17 was prepared in accord with the procedure described in Example 1 except using as starting material the compound of Preparation 34 rather than the compound of Preparation 2; m.p. 156–168° C. Anal. Calculated formula $C_{15}H_{19}NO_5 \cdot 1/4H_2O$: C, 60.04; H, 6.55; N, 4.70. Found: C, 60.07; H, 6.69; N, 4.56.

What is claimed is:

1. A compound of formula

I or a pharmaceutically acceptable salt thereof, wherein
  $R^1$ is selected from the group consisting of methyl, ethyl, difluoromethyl and trifluoromethyl;
  $R^2$ is $(C_1-C_6)$alkyl, $(C_3-C_7)$alkoxy$(C_2-C_4)$alkyl, phenoxy$(C_2-C_6)$alkyl, $(C_3-C_7)$cycloalkyl, $(C_6-C_9)$ polycycloalkyl, phenyl$(C_1-C_8)$alkyl or indanyl wherein the alkyl portion of said $R^2$ groups is optionally substituted with one or more fluorine atoms and the aryl portion of said $R^2$ groups is optionally substituted with one or more substituents independently selected from the group consisting of $(C_1-C_4)$alkyl, $(C_1-C_4)$ alkoxy and halogen;

AA is

54 wherein p ranges from 1 to 4; and
Y is NHOH or OH, with the proviso that when $R^1$ is methyl or ethyl and $R^2$ is $(C_1-C_6)$alkyl or $(C_3-C_7)$ cycloalkyl, then Y is NHOH.

2. The compound of claim 1 wherein $R^1$ is methyl.
3. The compound of claim 1 wherein $R^2$ is cyclopentyl.
4. The compound of claim 1, wherein p is 3.
5. The compound of claim 1 wherein Y is NHOH.
6. A pharmaceutical composition for inhibiting phosphodiesterase type IV or inhibiting the production of tumor necrosis factor in a mammal comprising a therapeutically effective amount of a compound according to claim 1 and a pharmaceutically acceptable carrier.
7. A pharmaceutical composition for treating a condition or disease selected from the group consisting of asthma, arthritis, bronchitis, chronic obstructive airways disease, psoriasis, allergic rhinitis, dermatitis, AIDS, septic shock and other conditions or diseases that respond to the inhibition of PDE type IV or the inhibition of the production of TNF in a mammal, comprising a therapeutically effective amount of a compound according to claim 1 and a pharmaceutically acceptable carrier.
8. A method of inhibiting PDE type IV or inhibiting the production of TNF in a mammal comprising administering to a mammal in need of such treatment a therapeutically effective amount of a compound according to claim 1.

9. A method of treating a condition or a disease selected from the group consisting of asthma, arthritis, bronchitis, chronic obstructive airways disease, psoriasis, allergic rhinitis, dermatitis, AIDS, septic shock and other conditions or diseases that respond to the inhibition of PDE type IV or the inhibition of the production of TNF in a mammal, comprising administering to a mammal in need of such treatment a therapeutically effective amount of a compound according to claim 1.

* * * * *